US006635419B1

(12) United States Patent
McGinnis et al.

(10) Patent No.: US 6,635,419 B1
(45) Date of Patent: Oct. 21, 2003

(54) POLYNUCLEOTIDE SEQUENCING METHOD

(75) Inventors: Malcolm D. McGinnis, Menlo Park, CA (US); Alex M. Madonik, Berkeley, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/250,422

(22) Filed: Feb. 16, 1999

(51) Int. Cl.⁷ .............................. C12Q 1/68; C12P 19/34; C07H 19/20
(52) U.S. Cl. .................. 435/6; 435/91.2; 536/26.2; 935/77; 935/78
(58) Field of Search ................... 435/6, 91.2; 536/26.6; 935/77, 78

(56) References Cited

U.S. PATENT DOCUMENTS

| 5,210,412 A | * | 5/1993 | Levis et al. ................. 250/288 |
| 5,470,705 A | | 11/1995 | Grossman et al. ............. 435/6 |
| 5,514,543 A | | 5/1996 | Grossman et al. ............. 435/6 |
| 5,580,732 A | | 12/1996 | Grossman et al. ............. 435/6 |
| 5,624,800 A | | 4/1997 | Grossman et al. ............. 435/6 |
| 5,654,442 A | | 8/1997 | Menchen et al. ........... 549/223 |
| 5,670,346 A | | 9/1997 | Reeve et al. ............. 435/91.53 |

FOREIGN PATENT DOCUMENTS

| EP | 252 683 A | 1/1988 |
| EP | 252 683 B1 | 1/1995 |
| EP | 805 190 A2 | 11/1995 |
| WO | WO 91/05060 | 4/1991 |
| WO | WO 92/06219 | 4/1992 |
| WO | WO 93/20236 | 10/1993 |
| WO | WO 98/38335 | 9/1998 |

OTHER PUBLICATIONS

Livak, K.J., et al., "Detection of Single Base Differences Using Biotinylated Nucleotides with Very Long Linker Arms" *Nucleic Acids Research* 20(18) :4831–4837 (1992).
Grossman, P.D., et al., "High–Density Multiplex Detection of Nucleic Acid Sequences" Oligonucleotide Ligation Assay and Sequence–Coded Separation *Nucleic Acids Research* 22 (21) :4527–4534 (1994).
Winn–Deen, E.S., "Multi–Mutation Screening Using PCR and Ligation—Principles and Applications" *Tibtech* 14:112–114 (1996).
Picketts, D.J., et al., "Differential Termination of Primer Extension: A Novel, Quantifiable Method for Detection of Point Mutations" *Human Genetics* 155–157 (1992).
Lee, L.G., et al., "DNA sequencing with dye–labeled terminators and T7 DNA polymerase: effect of dyes and dNTPs on incorporation of dye–terminators and probability analysis of termination fragments" *Nucleic Acids Research* (1992) 20(10) :2471–2483.
Lee, L.G. et al., "New energy transfer dyes for DNA sequencing" *Nucleic Acids Research* (1997) 25(14) : 2816–2822.
Rosenblum, B.B., et al., "New dye–labled terminators for improved DNA sequencing patterns" *Nucleic Acids Research* (1997) 25 (22) :4500–4504.

* cited by examiner

*Primary Examiner*—Ethan Whisenant
*Assistant Examiner*—Joyce Tung
(74) *Attorney, Agent, or Firm*—Vincent M. Powers; William D. Schmidt; Kalow & Springut LLP

(57) ABSTRACT

Disclosed is a method for determining a sequence of one or more nucleotides in a target polynucleotide. In the method, a target-specific primer is contacted with a polynucleotide sample under conditions effective for the primer to anneal specifically to a primer-complementary region in one or more target polynucleotides, to form one or more target-primer hybrid(s) wherein each target-specific primer contains (i) a target binding segment and (ii) a mobility-reducing moiety which does not bind the target. The hybrid (s) are reacted with a primer extension reagent in the presence of at least one labeled 3'-nucleotide terminator complementary to a selected nucleotide base-type, optionally in the presence of one or more extendable nucleoside monomers, under conditions effective to form one or more primer extension products which terminate with at least one labeled 3'-nucleotide terminator. The primer extension products are then separated electrophoretically in a sieving matrix under denaturing conditions such that smaller extension products migrate more rapidly than larger extension products, and the desired sequence information is determined.

32 Claims, No Drawings

POLYNUCLEOTIDE SEQUENCING METHOD

FIELD OF THE INVENTION

The present invention relates to methods for sequencing polynucleotides. In particular, the invention relates to an improved terminator sequencing method that expands the sequenceable range of bases adjacent to sequencing primers.

REFERENCES

Ausubel et al., eds., *Current Protocols in Molecular Biology* John Wiley & Sons, New York (1993).
Beaucage and Iyer, *Tetrahedron* 48:2223–2311 (1992).
Bergot, J. B., et al., PCT Pub. No. WO 91/05060 (1991).
Bergot, J. B., et al., U.S. Pat. No. 5,366,860 (1994).
Boom et al., U.S. Pat. No. 5,234,809.
Breslauer et al., *Proc. Natl. Acad. Sci.* 83:3746–3750 (1986).
Chidgeavadze et al., *FEB. Lett.* 183: 275–278 (1985).
Chidgeavadze et al., *Biochim. Biophys. Acta* 868:145 (1986).
Cohen, A. S., et al., *J. Chrom.* 516:49 (1990).
Dieffenbach et al., in *PCR Primer: A Laboratory Manual*, Dieffenbach and Dveksler, eds., pp. 133–142, CSHL Press, New York (1995).
Eckstein, F., *Oligonucleotides and Analogs: A Practical Approach*, Chapters 8 and 9, IRL Press, Oxford, GB (1991).
Fung et al, U.S. Pat. No. 4,757,141.
Gait, M. J., ed., *Oligonucleotide Synthesis: A Practical Approach*, IRL Press, Oxford (1984; 1990).
Gebeyehu et al., *Nucl. Acids Res.* 15:4513–4535 (1987).
Gibson et al., *Nucl. Acids Res.* 15:6455–6467 (1987).
Grossman, P. D., et al. U.S. Pat. No. 5,514,543 (1996).
Haralambidis et al., *Nucl. Acids Res.* 15:4856–4876 (1987).
Hartley, J. L., U.S. Pat. No. 5,035,996 (1991).
Haugland, *Handbook of Fluorescent Probes and Research Chemicals*, Molecular Probes, Inc., Eugene, Oreg. (1989).
Hobbs et al., U.S. Pat. No. 5,047,519 (1991).
Hobbs et al., U.S. Pat. No. 5,151,507 (1992).
Knudsen, H., et al., *Nucleic Acids Res.* 24:494–500 (1996).
Kornberg and Baker, *DNA Replication*, 2nd Ed., W.H. Freeman, San Francisco, Calif. (1992).
Krayevski, A., et al., *Biochim. Biophys. Acta* 783:216 (1984).
Lee, L. G., et al., *Nucl. Acids Res.* 20:2471–2483 (1992a).
Lee, L. G., PCT Pub. No. WO 92/06219 (1992b).
Lee, L. G., et al., EP Publication No. EP 805190 A2 (1997a).
Lee, L. G., et al., *Nucl. Acids Res.* 25:2816–2822 (1997b).
Longo, N., et al., Gene 93:125–128(1990).
Maniatis et al., *Meth. Enzymol.* 65:299–305 (1980).
Maniatis et al., *Biochemistry* 14:3787–3794 (1975).
Marra., M., et al., *Genomic Methods* 6:1118–1122 (1996).
Mathies, R. A., and Huang, X. C. *Nature* 359:167 (1992).
Maxam A. M., and Gilbert, W., *Proc. Natl. Acad. Sci.* 74:560∝564 (1977).
Menchen et al., PCT Publication No. WO 91/07507 (1991).
Menchen et al., PCT Publication No. WO 94/05688 (1994).
Mikhailopulo et al., *FEB Lett.* 250:139 (1989).
Miller et al., *Nucl. Acids Res.* 16:9-10 (1988).
Montpetit et al., *J. Virol. Methods* 36:119-128 (1992).
Mullis, K. B., U.S. Pat. Nos. 4,683,195 and 4,683,202.
Osborne, *CABIOS* 8:83 (1991).
Prober, J. M., et al., *Science* 238:336 (1987).
Prober, J. M., et al., EP Pat. No. 252683 B1 (1995).
Rosenblum et al., *Nucl. Acids Res.* 25:4500–4504 (1997).
Rychlik et al., *Nucleic Acids Res.* 17:8543–8551 (1989) and 18:6409–6412 (1990).
Sambrook et al., *Molecular Cloning: A Laboratory Manual* (Cold Spring Harbor Laboratory, New York, 1982), pp. 179–185 (1982).
Sanger, F., & Coulson, A. R., *Proc. Natl. Acad. Sci.* 74:5463–5467 (1977).
Scheit, *Nucleotide Analogs*, John Wiley Pub., New York (1980).
Smith et al. *Nature* 321:674–679 (1986).
Tabor, S., and Richardson, C. C., *J. Biol. Chem.* 264:6447 (1989).
Tabor, S., and Richardson, C. C., *J. Biol. Chem.* 265:8322 (1990).
Uhlman and Peyman, *Chem. Rev.* 90:543–584 (1990).
Walsh, *Biotechniques* 10:506–513 (1991).
Wetmur, *Crit. Rev. Biochem. Mol. Biol.* 26:227–259 (1991).
Zhu M. D., et al., U.S. Pat. No. 5,089,111 (1992).

BACKGROUND OF THE INVENTION

Sequence determination of polynucleotides is playing an increasingly important role in biochemical research and industry. For example, whole genomic sequences have been reported recently for the eukaryotes, *C. elegans* and *S. Cerevisiae* (e.g., see *Science* 282:2012 (1998)), and substantial efforts are currently underway to sequence the human genome. Knowledge of biological polynucleotide sequences is useful not only to characterize and compare gene sequences and associated gene products from different organisms, but also for the development of diagnostic tests, e.g., for detecting genetic mutations, determining genotypes, diagnosing disease, forensics, and identifying therapeutic targets.

Over the last two decades, there have been two principal approaches to nucleotide sequence determination: the chain termination method of Sanger and Coulson (1977), and the chemical degradation method of Maxam and Gilbert (1977). Both methods require the generation of one or more sets of labeled DNA fragments, each having a common origin and each terminating with a known base. The set or sets of fragments must then be separated by size to reveal the target sequence.

More recently, the chain termination method has become the standard method for all currently available automated DNA sequencing machines. This method generally involves enzymatic extension of a 5'-primer along a target template strand in the presence of the four standard deoxyribonucleotide bases, plus one or more dideoxynucleotide terminators. Incorporation of a terminator during primer extension results in a mixture of products of variable length, each terminating at its 3'-end with the terminator. As originally proposed, four separate sequencing reactions were performed for a given target sequence, one for each dideoxynucleotide base-type. The products from each mixture were then resolved in four separate lanes on the basis of size, and the target sequence was determined from the relative order of migration of the fragments.

Modifications to the Sanger method were subsequently developed which use spectrally distinguishable fluorescent labels attached to either the 5'-extension primers (Smith, 1986) or the 3'-dideoxy terminator bases (Prober, 1987; Prober 1995; Bergot, 1991). In the former case, extension reactions must be performed separately for each different terminator base in the presence of a suitably labeled primer (a different label for each different terminator), after which the labeled extension products can be combined and resolved in a single separation path. In the latter case, primer extension can be performed in a single reaction mixture, since base-specific label incorporation is performed with high fidelity by a polymerase enzyme, followed by separation in a single separation lane.

The labeled terminator method has become the sequencing method of choice because it involves significantly fewer reaction vessels and is more convenient to use. However, this method has been limited due to difficulty in routinely identifying sequencing fragment nucleotides close to the extension primers. The extension reactions require high concentrations of labeled terminators to ensure efficient production of sequencing fragments. Unfortunately, residual terminator bases or their breakdown products comigrate with short sequencing fragments because they have similar mobility properties. As a consequence, sequencing data for short sequencing fragments has been either unreliable or entirely unusable. Theoretically, it is possible to remove residual terminator bases prior to sequence analysis, e.g., by a preliminary size-based separation step. However, this introduces an extra step to the sequencing process that encumbers large-scale sequence analysis. Moreover, such preliminary purification may have to be repeated before enough residual terminator material has been removed.

Accordingly, it is an object of the present invention to provide a labeled terminator sequencing method that permits sequence determinations close to the extension primer.

A further object of the invention is to overcome the contamination problems that have been associated with previous labeled terminator sequencing methods.

SUMMARY OF THE INVENTION

The present invention provides, in one aspect, a method for determining a sequence of one or more nucleotides in a target polynucleotide. In the method, a target-specific primer is contacted with a polynucleotide sample under conditions effective for the primer to anneal specifically to a primer-complementary region in one or more target polynucleotides, to form one or more target-primer hybrid (s). The target-specific primer contains (i) a target binding segment and (ii) a mobility-reducing moiety which does not significantly bind to the target. The hybrid(s) are reacted with a primer extension reagent in the presence of at least one labeled 3'-nucleotide terminator complementary to a selected target nucleotide base-type, under conditions effective to form one or more primer extension products which terminate with at least one labeled 3'-nucleotide terminator. The primer extension products are then separated electrophoretically in a sieving matrix under denaturing conditions such that smaller extension products migrate more rapidly than larger extension products, and the desired sequence information is determined on the basis of the mobilities and terminator label(s) of the separated extension product(s).

In one embodiment, primer extension is performed in the presence of at least one extendable nucleoside monomer, in addition to the labeled 3'-nucleotide terminator(s), under conditions effective to extend the 3'-end of specifically hybridized primers by addition of target-complementary polynucleotide monomers and terminator(s), to form one or more primer extension products.

In another embodiment, primer extension is performed in the absence of extendable nucleotides, under conditions effective to append the terminator to the annealed primer in the hybrid only when the terminator is complementary to a base in the target polynucleotide that is immediately adjacent the extendable end of the annealed primer.

The terminator(s) used in the invention preferably include a label that can be detected during electrophoretic migration of the one or more extension products. In one embodiment, at least one 3'-nucleotide terminator contains a fluorescent label. In a preferred embodiment, extension is conducted in the presence of four different 3'-nucleotide terminators which (i) are each complementary to a different nucleotide base-type and (ii) each contain a distinguishable fluorescent label that identifies the base-type of the terminator.

For sequence determination, the sequencing extension products are separated on the basis of size by any method in which smaller fragments elute before larger fragments. For example, the products may be separated by slab gel electrophoresis, capillary electrophoresis, or microchannel electrophoresis, preferably using a sieving matrix.

In one embodiment, the mobility-reducing moiety comprises a polymer segment that does not substantially bind to the target polynucleotide(s). In one preferred embodiment, the polymer segment comprises a polynucleotide segment that does not substantially bind to the target polynucleotide (s). In other embodiments, the polymer segment comprises a nonpolynucleotide moiety, such as a nonpolynucleotide polymer of subunits.

The mobility-reducing moiety may be selected so as to decrease the mobility rate of each primer extension product by a specified amount. In one embodiment, the mobility-reducing moiety decreases the mobility rate of each primer extension product in an amount equivalent to at least 4 additional nucleotide bases, relative to the mobility of a corresponding primer extension product lacking the mobility-reducing moiety. In other embodiments, the amount of decrease in mobility is equivalent to the addition of at least 10 additional nucleotide bases, at least 15 additional nucleotide bases, or at least 20 additional nucleotide bases, according to the needs and design choice of the user.

The invention also includes a kit which is useful in practicing methods such as described above. The kit includes a target-specific primer that contains (i) a target binding segment and (ii) a mobility-reducing moiety which does not significantly bind the target. The kit may additionally include one or more of the following: at least one labeled nucleotide terminator, at least one extendable 3'-nucleoside, and a primer-extending reagent, such as a polymerase enzyme. The kit may also include instructions for utilizing the kit in accordance with the invention.

These and other objects and features of the invention will be more apparent in light of the discussion below.

DETAILED DESCRIPTION OF THE INVENTION

The present invention is directed to providing improved sequence reading capability for target sequence regions located adjacent to the 3'-end of a sequencing primer. For many terminator-based sequencing protocols, the ability to sequence target regions near the 3'-end of the sequencing primer is impeded due to interference from comigrating labeled 3'-terminators or their breakdown products. Although this problem can be reduced by removing residual terminators after primer extension is complete, more than one purification step is often required to obtain satisfactory results. It would therefore be advantageous if target regions near the primer, e.g., immediately adjacent to the 3'-end of the primer, could be easily sequenced without more than one pre-purification step to remove residual terminators.

This objective is achieved in the present invention by using a sequencing primer that contains a mobility-reducing moiety that reduces the mobility rates of the primer extension products, relative to the mobility rates of comparable extension products that are formed without the mobility-reducing moiety. By reducing the mobilities of the extension products, interference due to overlap with labeled terminators and their breakdown products can be reduced or eliminated because the terminators elute ahead of the primer-extension products. The invention therefore broadens the sequenceable regions of the primer extension products.

I. Definitions

As used herein, the terms below have the following meanings unless indicated otherwise:

"Nucleoside" refers to a compound containing a base-pairing moiety (also referred to as a"base"), such as a purine, deazapurine, or pyrimidine nucleoside base, e.g., adenine, guanine, cytosine, uracil, thymine, deazaadenine, deazaguanosine, or any functional equivalent thereof, which is attached to a backbone moiety such as a sugar ring or any functional equivalent thereof. Nucleosides include naturally occurring nucleosides which contain a base-pairing moiety (A, C, G, T or U) linked to the 1'-carbon of a pentose ring, including 2'-deoxy and 2'-hydroxyl forms thereof (Kornberg, 1992), and to pentose analogs and ring-open equivalents thereof (Scheit, 1980; Uhlman, 1990). For example, inosine (dITP) is often used in sequencing as a substitute for guanosine (dGTP) to reduce band compression in poly-G sequence regions.

The term"nucleotide" as used herein refers to a phosphate ester of a nucleoside, e.g., a triphosphate ester, wherein the most common site of esterification is the pentose 5'-hydroxyl group. In certain cases, term"nucleoside" refers both nucleosides and nucleotides, for convenience. The terms nucleotide and nucleoside as used herein are intended to include synthetic analogs having modified nucleoside base moieties, modified sugar moieties, and/or modified phosphate ester moieties, e.g., as described elsewhere (Scheit 1980; Eckstein, 1991).

"Polynucleotide" and"oligonucleotide" refer to a polymer of nucleoside monomers, including single, double and triple stranded deoxyribonucleotides, ribonucleotides, α-anomeric forms thereof, and the like. Usually the nucleoside monomers are linked by phosphodiester linkages, i.e., a phosphate diester or an analog thereof in which the phosphorous atom is in the +5 oxidation state and one or more of the oxygen atoms is replaced with a non-oxygen moiety. Exemplary phosphate analogs include phosphorothioate, phosphorodithioate, phosphoroselenoate, phosphorodiselenoate, phosphoroanilinothioate, phosphoranilidate, phosphoramidate, boronophosphates, and the like, including associated counterions, e.g., $H^+$, $NH_4^+$, $Na^+$, and the like, if such counterions are present. "Polynucleotides" and "oligonucleotide" also include polymers of non-nucleotidic monomers, linked by phosphate ester or other linkages, which are capable of forming sequence-specific hybrids with a target nucleic acid, e.g., peptide nucleic acids (PNAs; e.g., see Knudsen, 1996). Polynucleotides typically range in size from a few monomeric units, e.g. 8–40, to hundreds or thousands of monomeric units. Whenever a polynucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Primer" means a polynucleotide capable of selectively annealing to a specified target sequence and thereafter serving as a point of initiation of a primer extension reaction in the 5'→3' or 3'→5' direction.

"Primer extension reaction" means a reaction between a template-primer hybrid and one or more nucleotides which results in the addition of one or more nucleotides to a selected end of the primer such that the added nucleotide is complementary to the corresponding nucleotide in the target template nucleic acid.

"Extendable primer" refers to a primer that is capable of having a nucleotide appended (covalently linked) to an extendable end of the primer, typically the 3'-end of the primer.

"Target-specific primer" refers to a primer having a target-binding segment that is perfectly or substantially complementary to a target sequence, such that the primer binds specifically to an intended target without significant binding to non-target sequences under sufficiently stringent hybridization conditions.

"Nucleotide terminator" refers to a nucleotide or nucleoside that (1) is covalently linkable to an end of an extendible primer when the primer is annealed to a complementary template, but (2) is not capable of further extension under the conditions used to covalently link the nucleotide terminator to the primer.

"Specific binding pair" refers to a pair of molecules that specifically bind to one another to form a binding complex. Examples of specific binding pairs include, but are not limited to antibody-antigen (or hapten) pairs, ligand-receptor pairs, enzyme-substrate pairs, biotin-avidin pairs, polynucleotides having complementary base pairs, and the like.

"Primer extending reagent" means an enzyme or other catalyst capable of catalyzing a reaction leading to covalent attachment of a nucleotide terminator to an end of a primer when the primer is annealed to a complementary target nucleic acid.

"Label" means any moiety that, when attached to a nucleotide or polynucleotide of the invention, renders such nucleotide or polynucleotide detectable using known detection means.

A "sieving matrix" or "sieving medium" means an electrophoresis medium that contains crosslinked or non-crosslinked polymers which are effective to retard electrophoretic migration of charged species through the matrix, such that smaller extension products migrate more rapidly than larger extension products.

A. Sample Nucleic Acids

The target nucleic acids for use with the invention may be derived from any source, whether synthetic or natural, including but not limited to organisms such as prokaryotes, eukaryotes, plants, animals, and viruses, as well as synthetic nucleic acids. The target nucleic acids may originate from any of a wide variety of sample types, such as cell nuclei (e.g., genomic DNA) and extranuclear nucleic acids, e.g., plasmids, mitochondrial nucleic acids, and the like. The target polynucleotide may be obtained in single or double-stranded form according to known techniques. The target nucleic acids can include DNA or RNA, and are usually DNA.

Many methods are available for the isolation and purification of target nucleic acids for use in the present invention. Preferably, the target nucleic acids are sufficiently free of proteins and any other interfering substances to allow target-specific primer annealing and extension. Preferred purification methods include (i) organic extraction followed by ethanol precipitation, e.g., using a phenol/chloroform organic reagent (Ausubel), preferably using an automated DNA extractor, e.g., a Model 341 DNA Extractor from PE Biosystems (Foster City, Calif.); (ii) solid phase adsorption methods (Walsh, 1991; Boom); and (iii) salt-induced DNA precipitation methods (Miller), such methods being typically referred to as "salting-out" methods. Optimally, each of the above purification methods is preceded by an enzyme digestion step to help eliminate protein from the sample, e.g., digestion with proteinase K, or other like proteases.

To facilitate detection, the target nucleic acid may be amplified using a suitable amplification procedure prior to fragment analysis. Such amplification may be linear or exponential. In a preferred embodiment, amplification of the target nucleic acid is accomplished using the polymerase chain reaction (PCR) (Mullis). Generally, the PCR consists of an initial denaturation step which separates the strands of any double-stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon nucleic acid complementary to the target sequence, and (iii) a denaturation step which causes the separation of the amplicon from the target sequence. Each of the above steps may be conducted at a different temperature, preferably using an automated thermocycler (PE Biosystems, Foster City, Calif.).

In a preferred embodiment when a target amplification step is used, PCR amplification is performed in the presence of dUTP in place of dTTP, and amplification is preferably preceded by treatment with *E. coli* uracil N-glycosylase (UNG) to reduce carry over of templates from previous amplifications, as taught by Longo et al. (1990) and Hartley (1991). Conveniently, a kit for practicing this PCR technique is available from PE Biosystems (GENEAMP Carry-Over Prevention Kit, Part No. N808-0068). In brief, the initial reaction mixture for PCR amplification of target polynucleotide(s) is modified to include dUTP instead of dTTP. After addition of MgCl2 and DNA template, UNG enzyme is added (PE Biosystems, Part No. N808-0096), and the mixture is incubated at a temperature of up to 50° C. for a time sufficient (e.g., 1 to 10 minutes) to cleave U-containing PCR-amplified DNA contaminants from previous amplifications. The UNG enzyme does not cleave dUTP monomers. The mixture is then incubated at 95° C. for 10 minutes to (1) cleave any polynucleotides that contain abasic dU that were generated by UNG, (2) irreversibly inactivate the UNG, and (3) denature template DNA and primers. These conditions do not significantly inactivate a thermostable polymerase such as "AMPLITAQ" or "AMPLITAQ GOLD" (available from PE Biosystems). The mixture is then cycled through a selected number of PCR cycles until the desired amount of amplification has been obtained. A suitable thermocycler is a PE Biosystems "GENEAMP PCR INSTRUMENT SYSTEM". Preferably, the primer annealing temperature is greater than 55° C. to suppress the activity of any residual UNG enzyme. After the final cycle, the sample is preferably held at 72° C. until removal from the thermocycler. Upon removal, the mixture is preferably stored immediately at −20° C. or is treated with an equal volume of chloroform to denature any remaining UNG activity.

B. Sequencing Reagents

The present invention utilizes an extendable, target-specific primer, one or more labeled nucleotide terminators, and other reagents, for creating 3'-labeled primer extension products for sequencing. Selected reagents are discussed below.

1. Nucleotide terminators. Each nucleotide terminator is any nucleotide that is complementary to a selected polynucleotide base, such as A, C, G, T or U, and is also capable of being covalently linked to the 3'-end of the sequencing primer or growing primer extension product when the primer or extension product is specifically annealed to a target polynucleotide template. Thus, for covalent linkage to the 3'-end of a sequencing primer or extension product thereof, the nucleotide terminator (1) contains a suitable 5'-reactive group, such as a 5'-triphosphate moiety for reaction with a primer 3'-hydroxyl group, but the terminator (2) is incapable of further extension in the 3'-direction, e.g., by having a 3'-deoxy substituent or a 3'-hydroxy-blocking group in a ribose or deoxyribose ring instead of a 3'-hydroxyl group. Examples of 3'-deoxy substituents include hydrogen, 3'-fluoro, 3'-amino, and 3'-azido, for example (Mikhail-opulo et al., 1989; Krayevski et al., 1984; Chidgeavadze, 1986). Examples of 3'-hydroxy blocking groups include phosphate, phosphonate, t-Boc, and O-acetyl, for example. Exemplary nucleotide sugar moieties include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (e.g., Chidgeavadze, 1985).

Each nucleotide terminator includes a detectable label moiety for detecting sequencing primer extension products which contain the terminator. Labels may be direct labels which themselves are detectable or indirect labels which are detectable in combination with the use of secondary chemical agents. Exemplary direct labels include but are not limited to fluorophores, chromophores, radioisotopes (e.g., $^{32}P$, $^{35}S$, $^{14}C$, $^{3}H$), spin-labels, chemiluminescent labels, and the like. Exemplary indirect labels include enzymes which catalyze a signal-producing event, and ligands which are members of specific binding pairs, such as an antigen or biotin which can bind specifically with high affinity to a detectable anti-ligand, such as a labeled antibody or avidin Preferably, the label is a non-radioisotopic label. In a more preferred embodiment, the label is a fluorescent label or chemiluminescent label, and most preferably is a fluorescent label.

Isotopic labels can be introduced into terminators by known methods. For example, $^{32}P$ can be incorporated at the alpha phosphate position by 5'-phosphorylation of an appropriate 5'-activated nucleoside precursor. $^{35}S$ can be added to a 5'-alpha-phosphorus atom by known sulfurization processes. Methods for incorporating tritium or $^{14}C$ into nucleoside structures are also well known.

Non-isotopic labels can be incorporated into nucleoside analogs also by known methods. Typically, labels are attached to suitable substituent positions located in the nucleoside base, such as the 5-position of pyrimidines and the 7-position of 7-deazapurines (e.g., Prober, 1987, 1995; Menchen et al. 1991, 1994; Lee et al., 1992a,b)

A fluorescent label used in accordance with the present invention should have the following properties: (1) a distinguishable emission wavelength that makes the label easy to detect and distinguishable from other base-specific labels that may be present, (2) a narrow emission bandwidth, to reduce spectral overlap with other labels, (3) an absorption spectrum that is amenable to excitation by an inexpensive light source, such as an argon laser with emission peaks at 488 nm and 514 nm, (4) high quantum yield, meaning that fluorescent emission is the principal route of relaxation after excitation, (5) steric and chemical properties compatible with processing by a DNA or RNA polymerase, for appendage to a primer-extension fragment, and (6) stability to extension, separation, and detection steps.

Many useful fluorescently labeled nucleotide terminators have been described. Prober et al. (1987, 1995) discloses certain xanthene (succinyl fluoresceins) that can be used in a single extension reaction, followed by electrophoretic separation in a single lane. Additional, superior fluorescent labels are disclosed in Bergot et al. (1991; 1994) and Rosenblum et al. (1997) (9'-phenyl rhodamine backbone, with or without 4,7-dichloro substitution); Menchen et al. (1991; 1994) (4,7-dichlorofluoresceins); Lee et al. (1992a; 1992b) (fluorescein backbones); and Lee et al. (1997a,b) and Rosenblum et al. (1997) (4,7-dichlororhodamines ("dRhodamines"), and fluorescein-rhodamine donor-acceptor conjugates). The latter class of fluorescent labels are preferred because they can provide four-color dye sets with high spectral resolution and very high quantum efficiencies (~100%).

Labels can be readily attached to nucleotide bases, particularly the 5-position of pyrimidines and 7-position of deazapurines. Substitutions at these positions generally do not interfere with normal base-pairing of the associated bases and at the same time are acceptable for processing by various polymerases (Prober, 1995, page 17).

Generally, the linker can take on a number of different forms such that the length and rigidity of the linkage between the terminator base and label can vary greatly. For example, several suitable base labeling procedures have been reported that can be used, e.g., Gibson et al. (1987), Gebeyehu et al. (1987), Haralambidis et al. (1987), Haugland (1989), Menchen (1994), Lee et al. (1992b), and the like. In particular, fluorescein and rhodamine labels can be modified to include suitable functionalities, such as carboxyl, sulfonyl, isothiocyanate, succinimidyl carboxylate, phosphoramidite, amino, and methylamino (e.g., Menchen, 1994). In one embodiment, the linking group between the label and base is formed by reacting an N-hydroxysuccinimide (NHS) ester of a fluorescent label with an alkynylamino-derivatized base of a terminator (containing a 3-amino-1-propynyl linker), as taught by Prober et al. (1995) and Hobbs et al. (1991,1992), which are incorporated herein by reference. Longer linkers can also be used, such as the propynyl ethoxyamino linker described in Rosenblum et al. (1997), which was used to link the 5 or 6-carboxy groups of rhodamine compounds to the base moieties of ddT, ddC, and ddG. For donor-acceptor fluorescent labels (also sometimes called energy transfer dyes), the donor and acceptor may also be linked by a variety of linkers as described in Lee et al. (1997a) and Rosenblum et al. (1997), of which a 4'-aminomethylbenzoate-containing linker is preferred. Further details regarding various linking techniques can be found in Lee et al. (1992b). Prober et al. (Ibid), Rosenblum et al. (1997), and Lee et al. (1997a,b), for example.

2. Primers. The method of the invention preferably utilizes target-specific primers that contain (i) a target binding segment and (ii) a mobility-reducing moiety which does not bind the target. Primers can be prepared by any suitable method, preferably using an automated DNA synthesizer, e.g., PE Biosystems (Foster City, Calif.) model 392 or 394 DNA/RNA Synthesizer, using standard chemistries, e.g., phosphoramidite chemistry (Beaucage; Gait, 1984, 1990).

The sequence of the target binding segment of the primer is selected to hybridize to a selected complementary target sequence. Typically, the selected target sequence is a universal primer sequence from a cloning vector, such as a plasmid (e.g., m13 phage), into which the sample has been cloned. Alternatively, the target binding segment can be chosen to anneal to a conserved region upstream of a target locus to be sequenced, or to a unique target sequence upstream of a region of interest.

The length of the target binding segment is selected to ensure specific hybridization of the primer to the desired target, without significant cross-hybridization to non-target nucleic acids in the sample. Preferably, the melting temperature of the target binding segment is between 35 and 75 degrees Celsius, more. preferably between 50 and 70 degrees, and more preferably still between 55 and 65 degrees. A selected melting temperature can be achieved by suitable choice of base composition and binding segment length based on known methods for estimating primer melting temperatures (e.g., Breslauer, 1986; Rychlik, 1989 and 1990; Wetmur, 1991; Osborne, 1991; Montpetit, 1992). Typically, the target binding segment is between 15 and 30 bases in length. A target binding segment length between about 18 and 24 bases in length is usually preferred because such oligonucleotides tend to be very sequence-specific when the annealing temperature is set within a few degrees of a primer melting temperature (Dieffenbach, 1995).

The target binding segment is preferably designed to be extendable, meaning that a nucleotide monomer or terminator can be appended to one of the ends of the target binding segment when the target binding segment is hybridized to a complementary target sequence. Typically, the extendable end of the primer is located at the 3'-terminus of the target binding segment, such that the 3'-terminal base contains a 3'-hydroxyl, 3'-amino, or other reactive group that can be covalently linked to a nucleotide terminator by a primer extending reagent. Most typically, the 3'-end of the primer contains a 3'-terminal hydroxyl group.

As noted above, the sequencing primer additionally includes a mobility-reducing moiety which does not bind or hybridize significantly to the target polynucleotide. A major purpose of the mobility-reducing moiety is to reduce the rate of mobility of the sequencing extension products so that labeled terminator breakdown products elute before non-extended primer during electrophoretic separation. In particular, the mobility-reducing moiety may be selected so as to decrease the mobility rate of each primer extension product by a specified amount, e.g., by an amount equivalent to the presence of at least 10 additional nucleotide bases in the primer, relative to the mobility of a corresponding primer extension product lacking the mobility-reducing moiety.

In a first embodiment, the mobility-reducing moiety comprises a polynucleotide segment. The sequence of the polynucleotide is selected to be non-complementary towards the sample polynucleotide so that neither specific nor non-specific hybridization can occur with sample polynucleotides. For example, the segment can be homopolymeric (e.g., poly-C, G, A or T) or can contain dimeric repeats, such as poly(TC) (Example 1), poly(CA), or the like. The exact sequence of the mobility-reducing moiety will usually not be important as long as the sample does not contain a perfectly complementary sequence to the segment, and as long as target-specific annealing and primer extension can be performed reliably for sequence determination.

In a second general embodiment, the mobility-reducing moiety is a non-polynucleotidic polymer. The polymer may be a homopolymer or block copolymer, for example, and may have a linear, comb, branched, dendritic, or other architecture. Preferred polymers are those which are hydrophilic, or are at least sufficiently hydrophilic when bound to the target binding segment to ensure that the primer is readily soluble in aqueous media. The polymer should also not effect hybridization of the target binding segment to the target polynucleotide. Exemplary polymers can be prepared from ethylene oxide, glycolic acid, lactic acid, amino acid residues and polypeptides, saccharides and oligosaccharides, polyurethanes, polyamides, polysulfonamides, polysulfoxides, and block copolymers thereof, including polymers composed of units of multiple subunits linked by charged or uncharged linking groups. In a preferred embodiment, the mobility-reducing moiety is a polymer of ethylene oxide polymers, of the form $[—(OCH_2CH_2)_nOP(=O)(O^-)—]^m$, where n is 5 or 6, and m is 2 to 20 or more preferably is from 5 to 10. Such ethylene oxide-containing polymers can be prepared from pentaethylene oxide or hexaethylene oxide polymer blocks which are then converted to activated phosphoramidite derivatives, followed by sequential addition of a selected number of polymer block phosphoramidites to the 5'-terminal end of a target binding segment by standard phosphoramidite synthesis methods (e.g., see Grossman et al., 1996, at Examples 1 through 4).

Studies in support of the invention indicate that each unit of $-(OCH_2CH_2)_5OPO_2-$ decreases the mobility of an attached polynucleotide by the equivalent of about 2 additional nucleotides, and each unit of $-(OCH_2CH_2)_6OPO_2-$ decreases the mobility of an attached polynucleotide by the equivalent of about 2.5 additional nucleotides.

The mobility-reducing moiety can be attached to any part of the target binding segment, provided that the target binding segment permits primer extension along the intended target template. Most conveniently, the mobility-reducing moiety is joined to the 5'-end of the target binding segment of the primer. When the mobility-reducing moiety is a polynucleotide, the moiety can be readily incorporated into the primer by standard synthetic methods. Similarly, a non-polynucleotide mobility-reducing moiety can be added by standard conjugation methods, or can be built up on a target binding segment by stepwise addition of polymer-chain subunits to the binding segment using standard solid-phase synthesis methods. In addition, although the invention may be described herein with respect to a single polymer chain attached at a single site to an associated target binding segment, the invention also contemplates target binding segment which are derivatized by more than one polymer chain element, where the elements collectively form the polymer chain. Methods of synthesizing selected-length polymer chains are described, for example, in Grossman et al. (1996).

3. Primer-Extending Reagent. The primer-extending reagent can be any chemical or enzymic reagent that is effective to append nucleotide monomers to the extendable primer end which are complementary to the target template strand. In one embodiment, the primer extending reagent is a DNA polymerase enzyme. Exemplary polymerase enzymes include, but are not limited to, Pfu DNA polymerase, *E.Coli* polymerase I, T-7 polymerase, AMV reverse transcriptase, Taq DNA polymerase, AMPLITAQ DNA polymerase FS, Klenow fragment, Vent DNA polymerase, and the like (e.g., Kornberg and Baker). RNA polymerases and reverse-transcriptases can also be used, e.g., for RNA primers.

II. Method

In practicing the method of the invention, a selected polynucleotide sample is contacted with a target-specific primer under conditions effective for the primer to anneal specifically to a primer-complementary region in one or more target polynucleotides, to form one or more target-primer hybrid(s).

As discussed above, the target may be single or double stranded DNA, and may be prepared in accordance with known methods, e.g., by ultrafiltration using a "MICROCON-100" membrane from Amicon, Inc. (Beverly, Mass.), or using a "CENTRI-SEP" spin column (Princeton), or by treating the sample with shrimp alkaline phosphatase and exonuclease 1 (e.g., using a "PCR PRE-SEQUENCING KIT" from Amersham-Pharmacia Biotech). For larger DNA targets such as bacterial artificial chromosomes (BACs), it is preferred that DNA template be subjected to cesium chloride banding or to alkaline lysis (Marra et al., 1996), with extra phenol extraction and isopropanol precipitation steps if necessary. Commercial kits for BAC DNA preparation are also available (LigoChem., http://www.ligochem.com).

The annealing step is performed under conditions which are stringent enough to guarantee sequence specificity yet sufficiently permissive to allow formation of stable hybrids at an acceptable rate. The temperature and length of time required for. primer annealing depend upon several factors including the base composition, length and concentration of the primer, and the nature of the solvent used, e.g., the concentration of cosolvents such as DMSO (dimethylsulfoxide), formamide, or glycerol, and counterions such as magnesium or manganese. Typically, hybridization (annealing) is carried out at a temperature that is approximately 5 to 10° C. below the melting temperature of the target-primer hybrid in the annealing solution. Typically, the annealing temperature is in the range of 55 to 75° C. and the primer concentration is approximately 0.2 $\mu$M. Under such conditions, the annealing reaction is usually complete within a few seconds.

Following annealing of the primer to the target, the hybrid(s) are reacted with a primer extension reagent in the presence of at least one labeled 3'-nucleotide terminator complementary to a selected target nucleotide base-type, under conditions effective to form one or more primer extension products which terminate with at least one labeled 3'-nucleotide terminator.

In one embodiment, primer extension is performed in the absence of extendable nucleotides, under conditions effective to append the terminator to the annealed primer in the hybrid only when the terminator is complementary to a base in the target polynucleotide that is immediately adjacent the extendable end of the annealed primer. The sequence of the target binding segment of the primer is selected to hybridize to a selected complementary target polynucleotide which contains a potential polymorphic site located immediately adjacent to (immediately flanking) the terminal base at the extendable end of the primer. The target base to be detected can be any base that is sufficient to identify the presence of a polymorphism or mutation in a target polynucleotide, to identify a particular allele, or to exclude the presence of a potential target sequence. For example, in a genomic DNA target, the target base can be a single nucleotide polymorphism (SNP) that is associated with the occurrence of a particular disease, with an HLA type, or with any other genotypic or phenotypic trait. As further illustration, the target base can define (1) the terminus of a sequence insert; (2) the terminus of a remote region that has been spliced to the primer-complementary region in the target as the result of a deletion of one or more target bases; or (3) the terminus of a mis-spliced mRNA segment, for example. In some cases, the target polymorphism or mutation involves one of two possible alternative bases. Thus, reacting an annealed primer with the corresponding two complementary terminator bases in the presence of an extension reagent should be sufficient to identify at least one of the two possible alternative sequences. Similarly, if the target polymorphism is one of three or four possible alternatives, the annealed primer should be reacted with the appropriate number of possible base-type alternatives to confirm which possible sequences are actually present.

In another embodiment, primer extension is performed in the presence of at least one extendable nucleoside monomer, in addition to labeled 3'-nucleotide terminator(s), under conditions effective to extend the 3'-end of specifically hybridized primers by addition of target-complementary polynucleotide monomers and terminator(s), to form one or more primer extension products. Typically, extension is performed using four standard deoxyribonucleotide triphosphates (for A, C, G, T, including, for example, substituting dI for dG and dU for dT, if appropriate) and one, two, three, or preferably four different nucleotide terminators, terminator(s), to form one or more primer extension products, in order to provide sequence information for sequences having lengths of tens or several hundreds.

The concentrations of extendable nucleotides (if present) and labeled terminator will depend on the choice of polymerase and ther parameters according to known procedures (citations supra). In particular, terminator concentration can be optimized to take into account the signal intensities of the labels (if more than one label is used) and any variations in their rates of incorporation by the polymerase (e.g., see terminator concentrations disclosed in Table I of Rosenblum et al., 1997).

The reaction conditions used for primer extension may be any appropriate conditions chosen by the user and will generally depend on the amount of sample, the nature of the terminator(s), and the properties of the primer extension reagent. Preferably, the primer-extending reagent is a DNA or RNA polymerase, and the labeled nucleotide terminator contains a 5'-triphosphate group to facilitate covalent linkage to a 3'-hydroxyl group of the primer. Conditions for extending annealed primers using nucleic acid polymerases are well known (e.g., Ausubel, Sambrook). For example, the reaction conditions can be optimized according to known extension reagent cofactor requirements, pH dependencies, and buffer preferences. In particular, the choice of terminator type will often affect the choice of polymerase. For example, the xanthene-labeled terminators described in Prober (1995) are compatible with T7 DNA polymerase, AMV reverse transcriptase and bacteriophage T7 polymerase, but not with the Klenow fragment of DNA polymerase I. For the rhodamine-labeled terminators described by Bergot et al. (1991, 1994), Taq DNA polymerase is preferable. The modified T7 DNA polymerase of Tabor and Richardson (1989, 1990) are preferred for the fluorescein terminators described by Menchen et al. (1991; 1994) and Lee et al. (1992a,b). For the 4,7-dichlororhodamine terminators and rhodamine-fluorescein ("BIGDYE") energy transfer terminators described by Lee et al. (1997a,b) and Rosenblum et al. (1997),"AMPLITAQ DNA POLYMERASE FS" is usually preferred (PE Biosystems). Reaction conditions for primer extension using the above terminators are described in the above references and elsewhere or can be readily optimized by standard techniques.

The choice of primer, and particularly the choice of the mobility-reducing moiety, will depend on the type of labeled terminator(s) that are used and the mobilities of terminator breakdown products. For example, rhodamine-labeled terminators contain a resonance-stabilized positive charge shared by the 3- and 6-nitrogen atoms, which retards the mobility of the terminators relative to the corresponding non-labeled terminators. Thus, rhodamine terminators and their breakdown products can comigrate with short primer extension products and interfere with sequences determinations. Similarly, the "BIGDYE" rhodamine/fluorescein terminators described by Lee et al. (1997) and Rosenblum et al. (1997) give rise to breakdown products that can interfere with short primer extension products, due to the presence of the positively charged rhodamine moieties. Finally, although fluorescein terminators usually migrate ahead of the sequencing primers (due to the presence of a resonance stabilized negative charge shared by the 3- and 6-oxygen atoms), dephosphorylation and cleavage of the base moieties can give rise to breakdown products that overlap with extension products. Accordingly, the length of the mobility-reducing moiety in the primer is selected to ensure that primer extension products of a certain length range, and preferably all primer extension products, can be sequenced in a region of interest without interference from labeled terminators or terminator breakdown products. In certain preferred embodiments, the mobility-reducing moiety is selected to decrease the mobility rate of each primer extension product by an amount equivalent to at least 4 or at least 10 additional nucleotide bases, relative to the mobility of a corresponding primer extension product lacking the mobility-reducing moiety, or by an amount equivalent to the addition of at least 15 additional nucleotide bases, or by an amount equivalent to the addition at least 20 additional nucleotide bases.

In one embodiment, in which one or more extendable nucleotides are used, primer extension is accomplished by dividing the hybridization mixture into two or more aliquots, and each aliquot is reacted with a different, single nucleotide terminator base-type. For example, the hybridization mixture can be divided into four aliquots, and each aliquot is reacted with a selected terminator equivalent to A, C, G or T/U. Using this approach, all terminators can contain the same label, provided that the extension reactions for each different terminator type are kept separate from each other during primer extension and electrophoretic separation. Preferably, the hybridization mixture is reacted simultaneously in the same mixture with a set of four terminator types encompassing A, C, G and U/T, and which have distinct labels to identify each terminator type.

According to various embodiments of the invention, multiple cycles of primer extension can be performed in the reaction mixture using known methods (cycle sequencing), to increase the levels of extension products for analysis. Thus, after a first extension reaction, primers (extended and non-extended) can be denatured from the target polynucleotides by appropriate means (e.g., by heating the extension reaction well above the melting temperatures of the extension products), followed by annealing of new, non-extended primers onto the target polynucleotides and primer extension. Since the non-extended primers are usually present in excess relative to the target polynucleotides, the amount of extended primers that reanneal to the target polynucleotides is usually insignificant. For example, an extension mixture can be cycled through multiple cycles (e.g., 10 to 50) comprising (1) heat at 95° C. for 10 sec (denaturation), 45° C. for 5 sec (primer annealing), and 60° C. for 1 to 5 minutes (extension)

After formation of primer extension products has been completed, the product mixture is optionally purified to remove residual terminators and terminator by-products and other reaction components prior to electrophoretic separation. Such purification step(s) may be useful for reducing the bulk of labeled terminator products from the sample. However, the benefits of purification will generally decrease with the number of purification steps. Also, purification steps increase the cost and time of sequencing, and can reduce the signal due to loss of extension products.

Any suitable purification method(s) may be used, such as gel filtration, ethanol precipitation, or isopropanol precipitation, according to known techniques (e.g., see the protocol entitled "ABI PRISM BIGDYE Terminator Cycle Sequencing Ready Reaction Kit available from PE Biosystems (1998), Foster City, Calif.). For example, gel filtration is preferably accomplished using a "CENTRI-SEP" spin column from Princeton Separations (P/N CS-901). The column should be loaded carefully above the center of the column bed without dripping down the interior side of the column. After loading, the column is preferably spun at 325–730×g for less than 2 minutes. The filtrate contains the desired extension products which can be dried in a microfuge for subsequent separation. Ethanol precipitations are preferably performed with sodium acetate. For example, 50 $\mu$L of non-denatured 95% ethanol and 2 $\mu$L of 3 M sodium acetate (pH 4.6) can be added to about 20 $\mu$L of an extension reaction mixture in a sealable tube to produce a final volume of 72 $\mu$L containing about 65% ethanol. Higher and lower ethanol concentrations can also be used. The tube is then sealed (e.g., with a piece of 3M "SCOTCH TAPE" 425-3 adhesive-backed aluminum foil tape, and is inverted a few times to mix (or is mixed by pipetting). The tube is allowed to sit at room temperature for 15 minutes to preferentially precipitate the extension products. The tube is then centrifuged at 1400 to 3000×g for 30 to 45 minutes to pellet the precipitate. After centrifugation, the adhesive tape is removed immediately without disturbing the pellet, and the supernatant is removed by inverting the tube onto a paper towel. The inverted tube with paper towel is placed into a centrifuge and spun at 700×g for 1 minute. The pellet may be rinsed with 50 to 100 $\mu$L of 70% ethanol of 70% ethanol, followed by brief vortexing, centrifugation, removal of supernatant, and drying the pellet.

According to another advantage of the invention, the presence of a mobility reducing moiety, e.g., a polynucleotide segment, can improve the recovery of short primer extension products from ethanol precipitation. Typically, the recovery of extension products is dependent on ethanol concentration. Lower ethanol concentrations tend to precipitate lower amounts of terminators and terminator breakdown products. However, the recovery of short primer extension products may also be reduced. On the other hand, although higher ethanol concentrations can increase the amount of precipitated short extension products, precipitation of unreacted terminators and terminator breakdown products may also be increased, leading to increased noise in the resulting electropherograms. Studies conducted in support of the invention show that short extension products produced with primers that contain a mobility reducing moiety are more readily precipitated by ethanol precipitation than are corresponding extension products which lack the mobility reducing moiety. Thus, lower ethanol concentrations can be used to selectively precipitate extension products while unreacted terminators remain in the supernatant. Accordingly, signals produced by labeled terminators and terminator breakdown products can be further reduced so that sequencing of short extension products is further simplified.

Extension products can be separated electrophoretically under denaturing conditions in a sieving matrix such that smaller extension products migrate more rapidly than larger extension products. Sieving matrices which can be used include covalently crosslinked matrices, such as acrylamide covalently crosslinked with bis-acrylamide (Cohen et al., 1990); gel matrices formed with linear polymers (Matthies et al., 1992); and gel-free sieving media (Zhu et al. 1992), for example. Preferably the type of electrophoretic matrix is crosslinked or noncrosslinked polyacrylamide having a concentration (weight to volume) of between about 2–20 weight percent. More preferably, the polyacrylamide concentration is between about 4–8 percent. The separation matrix may additionally includes a denaturing agent, e.g., 7 M urea, formamide, or the like. Detailed procedures for constructing such matrices are given by Maniatis et al. (1975, 1980) and Sambrook et al. (1982, 1989). The optimal polymer concentration, pH, temperature, concentration of denaturing agent, etc. employed in a particular separation depends on factors such as the size range of the extension products to be separated, number of different length fragments, and their base compositions. Accordingly application of the invention may require preliminary testing to optimize conditions for particular separations.

The configuration of the separation medium can be any suitable configuration selected by the user. Typical configurations include vertical or horizontal slab gels, capillary electrophoresis tubes, and channels formed in a substrate such as a glass or silicon substrate. For example, a capillary tube or microchannel will typically define an electrophoretic path that having an inner diameter of 200 $\mu$m or less, and more preferably 100 $\mu$m or less.

During or after separation of the extension products, a target sequence can be determined from the order of migration of the separated extension products. Any detection method may be used which is suitable for the type of label employed. Exemplary detection methods include radioactive detection (e.g., using a CCD or phosphorimager), optical absorbance detection, e.g., UV-visible absorbance detection, and optical emission detection, e.g., fluorescence or chemiluminescence.

According to one preferred embodiment, the different extension products are detected directly, without requiring reaction of the fragments with an additional chemical entity to enable detection. For example, fluorescently labeled extension products can be read directly while still in a slab gel or capillary tube as noted above.

In particular, fluorescently labeled extension products can be detected by measuring the fluorescence emission from dye-labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or the 532 nm emission line of a neodymium solid-state YAG laser. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g., a photomultiplier tube, a charged coupled device, or the like. Exemplary commercially available systems for sequencing include an ABI PRISM 310 (capillary electrophoresis) and 377 (slab gel electrophoresis) DNA Sequencers (PE Biosystems). Additional guidance regarding various modes of detection for sequence determination can be found in Prober et al. (1995), Rosenblum et al. (1997), and Lee et al. (1997a,b). Base-calling software is available from numerous commercial sources to further simplify sequence determinations. Such software preferably includes algorithms for correcting mobility shifts caused by labeled terminators.

When sequencing is conducted using four extendable nucleotide monomers and four differently labeled terminators (or four different terminators that contain the same label, which are prepared and electrophoretically separated in separate lanes), a sequence of contiguous bases can be readily determined by collating the orders of migration of fragments containing the four different terminators. However, using fewer than four different terminators can also provide useful information in the form of electrophoretic signatures or fingerprints (i.e., fragments that terminate with T) that can identify the presence or absence of an expected sequence.

For heterozygous samples, sequence information can be obtained by deconvolution of overlapping sequences if the contributing allelic sequences are known and are sufficiently distinguishable from each other. Otherwise, it may be necessary to utilize separately one or more allele-specific primers that selectively hybridize to a subset of allelic sequences to simplify analysis of the extension products. For embodiments that utilize labeled terminators in the absence of extendable nucleotide monomers, heterozygous samples can typically be characterized based on the presence of two possible base-types in equal amounts.

III. Sequencing Kits

In another aspect, the invention includes kits and reagents that may be used in any of the above methods. In one embodiment, the invention includes a kit that comprises a target-specific primer that contains (i) a target binding segment and (ii) a mobility-reducing moiety which does not significantly bind the target. The kit may additionally include one or more of the following: (b) at least one labeled nucleotide terminator, (c) at least one extendable 3'-nucleoside, (d) a primer-extending reagent, such as a polymerase enzyme. The kit may also include instructions for utilizing the kit in accordance with the invention. Preferably, at least one labeled nucleotide terminator is a 2',3'-dideoxymononucleotide. In a preferred embodiment, the kit includes four differently labeled nucleotide terminators which are complementary to adenine, guanine, cytosine, and either thymine or uracil bases. The kit can also include four extendable 3-nucleosides which are complementary to A, G, C, and U/T.

From the foregoing, it can be seen how the objects and features of the invention are met. The invention provides an improved dye-terminator polynucleotide sequencing method which avoids the problems resulting from comigration of dye-terminators and terminator breakdown products with short primer extension products. The invention allows sequencing of polynucleotide regions near the extension primer, which can be important for distinguishing polymorphic variants. Furthermore, the invention effectively expands the polynucleotide length range that are sequenceable by dye-terminator based sequencing methods. The invention is thus particularly useful for sequencing single polynucleotide targets or heterozygous polynucleotide targets by direct labeling methods, in which sequence information is derived while the extension products are in the separation medium or are just exiting from the medium (e.g., real time monitoring during electrophoresis, or by scanning migration patterns within one or more lanes across a selected length range in the gel), without requiring reaction of the extension products with a secondary reagent for detection.

The invention may be further understood in light of the following examples, which are not intended to limit the scope of the invention.

EXAMPLE 1

A sample containing the human HLA-DRB locus was sequenced following the protocols described in the protocol booklet for the "HLA-DRB BIGDYE TERMINATOR SEQUENCING-BASED TYPING KIT" (PE Biosystems, 1998) using two codon-86 GGT-specific primers for HLA-DRB Exon 2 (reverse orientation). The two primers had the following sequences, wherein the second primer includes a poly d(TC) mobility-reducing moiety 24 bases in length:

SEO ID NO:1 (primer 1)
  GCA CTG TGA AGC TCT CAC C
SEO ID NO:2 (primer 2)
  TCT CTC TCT CTC TCT CTC TCT CTC GCA CTG TGA AGC TCT CAC C Primer extension reactions were conducted using one or the other of these primers alone and either (1) a mixture containing four BIGDYE terminators designated ddT-EO-6CFB-dTMR, ddG-EP-5CFB-dR110, ddC-EO-6CFB-dROX, and ddA-PA-6CFB-dR6G (BIGDYE Ready Reaction Premix from PE Biosystems) or (2) a mixture containing four dRhodamine terminators designated ddT-EO-6dROX, ddG-EO-5dR10, ddC-EO-5dTMR, and ddA-PA-5dR6G (Rhodamine Ready Reaction Premix from PE Biosystems) following the procedure described in the protocol entitled "ABI PRISM BIGDYE Terminator Cycle Sequencing Ready Reaction Kit available from PE Biosystems (1998). After the extension reaction but before electrophoresis on an ABI PRISM Model 377 DNA Sequencer, the primer extension product mixture (10 μL) was mixed 30 μL of 100:4 (v:v) mixture of 100% ethanol:sodium acetate (3 M, pH 4.6). The results were as follows.

For the extension reaction using BIGDYE terminators and primer 1, several large residual (unincorporated) terminator peaks comigrated with the 27 fastest-migrating extension products, so that determining the sequence of about the first 30 target bases past the primer was not possible. In contrast, for the extension products that were formed using the BIGDYE terminators and primer 1, the same residual terminator peaks migrated in a window of about 3 to 27 bases ahead of the most quickly migrating extension product (primer plus extension one base). Very little if any terminator peaks comigrated with the primer extension products, so that all primer extension products were readable, including the first 20 target nucleotide bases.

For the dRhodamine extension products, the use of primer 2 was effective to cause several two major terminator peaks to migrate about 5 to 8 bases ahead of the fastest migrating primer extension product. In addition, several other small terminator peaks also migrated ahead of the fastest migrating primer extension product, so that the entire target sequence could be readily determined, including the first 20 target bases. In contrast, the use of primer 1 led to comigration of several large terminator peaks within the first 20 primer extension products, so that several of the first 20 target bases could not be determined.

This study was repeated that 25 μL of ethanol:sodium acetate mixture was used instead of 30 μL. This modification was effective to reduce the amplitudes of the residual terminator peaks in all cases. However, for primer extension products formed with primer 1, levels of the ~20 fastest migrating extension products were substantially reduced, so that the first 20 target bases were difficult or impossible to determine. In contrast, signals for extension products containing primer 2 were strong even for the 20 fastest migrating extension products, due to efficient ethanol precipitation of these species.

Overall, these results demonstrate that the method of the present invention is advantageous for improving readability of short primer extension products, especially the first 20 target bases.

Although the invention has been described with respect to particular embodiments, it will be appreciated that various modifications can be made without departing from the invention. All references cited above are incorporated herein by reference in their entirety.

cally hybridized primers by addition of target-complementary polynucleotide monomers and terminator(s), to form said one or more extension products.

3. The method of claim 1, wherein primer extension is performed in the absence of extendable nucleoside monomers, under conditions effective to append the at least one labeled 3-nucleotide terminator to at least one specifically annealed primer only when the terminator is comple-

What is claimed is:

1. A method for determining a sequence of one or more nucleotides in a target polynucleotide, the method comprising:
    contacting a target-specific primer with a polynucleotide sample under conditions effective for the primer to anneal specifically to a primer-complementary region in one or more target polynucleotides, to form one or more target-primer hybrid(s), wherein each target-specific primer contains (i) a target binding segment and (ii) a mobility-reducing moiety which does not bind the target,
    reacting said hybrid(s) with a primer extension reagent in the presence of at least one labeled 3'-nucleotide terminator complementary to a selected nucleotide base-type, under conditions effective to form one or more primer extension products which tenninate with at least one labeled 3'-nucleotide terminator that produces a detectable signal,
    separating electrophoretically the primer extension product(s) under denaturing conditions in a sieving matrix such that (i) smaller extension products migrate more rapidly than larger extension products and (ii) at least one detectable breakdown product from the labeled 3'-nucleotide terminator elutes before non-extended primer so as not to overlap in elution with said primer extension product(s), and
    detecting at least one detectable signal from said separated primer extension product(s) to determine a target sequence on the basis of the mobilities and detectable signals from the separated extension product(s).

2. The method of claim 1, wherein primer extension is performed in the presence of at least one extendable nucleoside monomer under conditions effective to extend specifimentary to a base in the target polynucleotide that is immediately adjacent the extendable end of the annealed primer.

4. The method of claim 1, wherein at least one 3'-nucleotide terminator contains a fluorescent label.

5. The method of claim 4, wherein said reacting is conducted in the presence of four different 3'-nucleotide terminators which (i) are each complementary to a different nucleotide base-type and (ii) each contain a distinguishable fluorescent label that identifies the base-type of the terminator.

6. The method of claim 1, wherein said separating is performed by slab gel electrophoresis.

7. The method of claim 1, wherein said separating is performed by capillary electrophoresis.

8. The method of claim 1, wherein said separating is performed in a microchannel.

9. The method of claim 1, wherein at least one 3'-nucleotide terminator contains a radioactive label.

10. The method of claim 1, wherein said mobility-reducing. moiety comprises a polymer segment that does not substantially bind to the target polynucleotide(s).

11. The method of claim 10, wherein said polymer segment comprises a polynucleotide segment that does not substantially bind to the target polynucleotide(s).

12. The method of claim 1, wherein said mobility-reducing moiety is effective to decrease the mobility rate of each primer extension product in an amount equivalent to at least 10 additional nucleotide bases, relative to the mobility of a corresponding primer extension product lacking the mobility-reducing moiety.

13. The method of claim 12, wherein the amount of said decrease in mobility is equivalent to the addition of at least 15 additional nucleotide bases.

14. The method of claim 13, wherein the amount of said decrease in mobility is equivalent to the addition of at least additional nucleotide bases.

15. The method of claim 4, wherein primer extension is performed in the presence of at least one extendable nucleoside monomer under conditions effective to extend specifically hybridized primers by addition of target-complementary polynucleotide monomers and terminator(s), to form said one or more extension products.

16. The method of claim 15, wherein said mobility-reducing moiety comprises a polymer segment that does not substantially bind to the target polynucleotide(s).

17. The method of claim 16, wherein said mobility-reducing moiety is effective to decrease the mobility rate of each primer extension product in an-amount equivalent to at least 10 additional nucleotide bases, relative to the mobility of a corresponding primer extension product lacking the mobility-reducing moiety.

18. The method of claim 17, wherein the amount of said decrease in mobility is equivalent to the addition of at least 15 additional nucleotide bases.

19. The method of claim 18, wherein the amount of said decrease in mobility is equivalent to the addition of at least 20 additional nucleotide bases.

20. The method of claim 16, wherein said polymer segment comprises a polynucleotide segment that does not substantially bind to the target polynucleotide(s).

21. The method of claim 20, wherein said mobility-reducing moiety is effective to decrease the mobility rate of each primer extension product in an amount equivalent to at least 10 additional nucleotide bases, relative to the mobility of a corresponding primer extension product lacking the mobility-reducing moiety.

22. The method of claim 21, wherein the amount of said decrease in mobility is equivalent to the addition of at least 15 additional nucleotide bases.

23. The method of claim 22, wherein the amount of said decrease in mobility is equivalent to the addition of at least 20 additional nucleotide bases.

24. The method of claim 4, wherein primer extension is performed in the absence of extendable nucleoside monomers, under conditions effective to append the at least one labeled 3-nucleotide terminator to at least one specifically annealed primer only when the terminator is complementary to a base in the target polynucleotide that is immediately adjacent the extendable end of the annealed primer.

25. The method of claim 24, wherein said mobility-reducing moiety comprises a polymer segment that does not substantially bind to the target polynucleotide(s).

26. The method of claim 25, wherein said mobility-reducing moiety is effective to decrease the mobility rate of each primer extension product in an amount equivalent to at least 10 additional nucleotide bases, relative to the mobility of a corresponding primer extension product lacking the mobility-reducing moiety.

27. The method of claim 26, wherein the amount of said decrease in mobility is equivalent to the addition of at least 15 additional nucleotide bases.

28. The method of claim 27, wherein the amount of said decrease in mobility is equivalent to the addition of at least 20 additional nucleotide bases.

29. The method of claim 28, wherein said polymer segment comprises a polynucleotide segment that does not substantially bind to the target polynucleotide(s).

30. The method of claim 29, wherein said mobility-reducing moiety is effective to decrease the mobility rate of each primer extension product in an amount equivalent to at least 10 additional nucleotide bases, relative to the mobility of a corresponding primer extension product lacking the mobility-reducing moiety.

31. The method of claim 30, wherein the amount of said decrease in mobility is equivalent to the addition of at least 15 additional nucleotide bases.

32. The method of claim 31, wherein the amount of said decrease in mobility is equivalent to the addition of at least 20 additional nucleotide bases.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Homo sapiens

<400> SEQUENCE: 1
gcactgtgaa gctctcacc                                                19

<210> SEQ ID NO 2
<211> LENGTH: 43
<212> TYPE: DNA
<213> ORGANISM: Homo sapiens

<400> SEQUENCE: 2
tctctctctc tctctctctc tctcgcactg tgaagctctc acc                      43